United States Patent [19]

Weiss

[11] Patent Number: 4,870,689

[45] Date of Patent: Sep. 26, 1989

[54] EAR WAX BARRIER FOR A HEARING AID

[75] Inventor: Erwin W. Weiss, Northbrook, Ill.

[73] Assignee: Beltone Electronics Corporation, Chicago, Ill.

[21] Appl. No.: 170,023

[22] Filed: Mar. 31, 1988

Related U.S. Application Data

[63] Continuation-in-part of Ser. No. 37,330, Apr. 13, 1987, abandoned.

[51] Int. Cl.⁴ ...................... H04R 25/02; A61F 11/02

[52] U.S. Cl. .................................. 381/68.6; 128/867; 181/135; 381/69

[58] Field of Search ................. 381/68.6, 68, 69, 68.7; 181/135; 128/151, 152, 864, 867, 857

[56] References Cited

U.S. PATENT DOCUMENTS

| | | | |
|---|---|---|---|
| Re. 26,174 | 3/1967 | Leale | 381/68.6 |
| 3,170,046 | 2/1965 | Leale | 381/68.6 |
| 3,197,577 | 7/1965 | Kuklock | 381/68.6 |
| 3,374,318 | 3/1968 | Martin | 381/68.6 |
| 3,414,685 | 12/1968 | Geib et al. | 381/68.6 |
| 4,447,677 | 5/1984 | Miyahra et al. | 381/68.7 |
| 4,520,236 | 5/1985 | Gauthier | 381/69 |
| 4,679,650 | 7/1987 | Moser et al. | 181/135 |

FOREIGN PATENT DOCUMENTS

| | | | |
|---|---|---|---|
| 1263849 | 3/1968 | Fed. Rep. of Germany | 381/68.6 |

*Primary Examiner*—Jin F. Ng
*Assistant Examiner*—Danita R. Byrd
*Attorney, Agent, or Firm*—Allegretti & Witcoff, Ltd.

[57] ABSTRACT

An ear wax barrier for a hearing aid to prevent ear wax from contacting and damaging the internal components of a hearing aid or hearing aid receiver. The barrier includes a housing defining a central axis of passage, as well as a plurality of projections and a variable acoustic attenuator. The projections extend inwardly from the interior surface of the housing, each projection partially occluding the cross-sectional area of the housing. The projection provides a tortuous path for ear wax migrating into the hearing aid. The variable acoustic attenuator and the projections provide a constricted passageway for damping of the acoustic response of the hearing aid.

6 Claims, 5 Drawing Sheets

EAR WAX BARRIER FOR A HEARING AID

CROSS REFERENCE TO RELATED APPLICATION

This application is a continuation-in-part application of prior co-pending application Ser. No. 037,330, filed Apr. 13, 1987, now abandoned, the contents of which are incorporated herein by reference thereto.

BACKGROUND OF THE INVENTION

The present invention relates generally to an ear wax barrier and more particularly to a barrier for preventing ear wax from entering the sound channel of a hearing aid and device, such as "in-the-ear" or "canal" type hearing aids or acoustical resonators.

Most hearing aids include a housing, or shell, that holds the components of the aid. The shell of many aids is designed to rest within the ear canal of a user. The shell of an electronic hearing aid may hold, for example, a microphone, amplification circuitry, and a receiver. The microphone is exposed to sound signals from outside of the aid and responsively creates an electrical signal. The electrical signal may be sent to the amplifying circuitry or other electrical aid components. Such components, in turn, supply a signal to the receiver, and the receiver responsively creates sound.

In many electronic hearing aids, the sound travels from an output port of the receiver, through a sound channel in the aid, and out of the aid through an output port in the shell of the aid. The sound from the shell output port may then travel through the user's ear canal and cause the ear drum to vibrate.

The ears of most hearing aid users naturally secrete a substance referred to as cerumen or ear wax. While the ear wax cleans the internal structure of an ear, it also tends to flow into the sound channel and receiver of the hearing aid. Upon entering the receiver, the ear wax interferes with, or prevents, the proper operation of the receiver.

Small, cosmetic "in-the-ear" aids and "canal" aids (which typically lay at least partially within the user's ear canal) have recently been developed. With such aids, however, the volume inside of the hearing aid available for components is reduced. This is particularly true, for example, when the interior of the user's ear is relatively small.

Furthermore, the technology associated with hearing aid manufacture frequently involves fabricating the shell out of plastic. The shell is contoured to the shape of the inner surface of the ear. The thickness of the shell is dictated by the requirement that the shell physically maintain its structural integrity and protect the aid components inside. The wall thickness of the shell, however, reduces the volume inside the hearing aid available for components.

The resulting limited volume within the hearing aid available for components generally requires that the receiver be positioned as deep as possible in the user's canal. However, such positioning of the hearing aid within the canal brings the receiver output port into closer proximity to the ear canal environment containing the wax-generating tissue inside the ear canal.

Thus, while the introduction of in-the-ear and canal aids has improved the acceptance of hearing aids by the hearing-impaired public, such hearing aids have created a problem of dealing with ear wax. As those of the ordinary skill in the art will acknowledge, ear wax migration has been recognized as a difficult problem.

The migration of wax into the sound channel and receiver of hearing aids substantially increases the susceptibility of many receivers to clogging. The progressive, gradual clogging of the receiver results in the reduction of acoustic gain and in power output by the receiver, sometimes culminating in the complete failure of the aid to allow output of amplified sound.

The degradation or failure of performance of the aid is annoying to the user. When wax blockage occurs, the hearing aid may require complete disassembly so that the receiver may be cleaned or replaced. Of course, bringing the hearing aid to a service center for disassembly and possible replacement of the receiver is both inconvenient and expensive for the user.

A number of presently available systems are poorly suited to guard against ear wax buildup in the receiver of a hearing aid. Some "barrier" designs use a fine mesh screen in the sound channel between the receiver and the outside of the hearing aid. Such screens suffer from the deficiency, however, that if the screen size is made sufficiently small to protect the receiver from wax migration, the screen holes will eventually be clogged by the wax. When mesh is made more coarse, however, wax will not as effectively be prevented from migrating across the screen barrier to the receiver.

Other systems for preventing wax migration into a receiver include providing a single aperture, of a small cross sectional area, between the receiver and the outside of the aid. Other systems involve the replacement of a cellular synthetic material between the receiver and outside of the aid. Such designs often suffer from the same deficiency in achieving simultaneously both a long-term barrier to wax migration as well as still preventing the clogging of wax over the life of the aid.

Such porous barriers, thus, generally result in an unsatisfactory trade-off between resistance to wax clogging of the barrier itself, on the one hand, and the prevention of wax migration into the receiver on the other. While a small aperture barrier may prevent wax migration, it will also clog. Large apertures may not clog, but they also will not be as effective in blocking wax.

Moreover, small pore barriers placed in the pathway between the receiver and the output port of the hearing aid may cause increased acoustic impedance. Increased impedance may result in an undesired change in the frequency response in output pressure levels delivered by the receiver.

SUMMARY OF THE INVENTION

A principal aspect of the present invention is an ear wax barrier for a hearing aid. For illustrative purposes, the invention is particularly described herein as used with an electronic hearing aid. However, those skilled in the art will understand that the invention also is useful with acoustical resonators, acoustical hearing aids and in other ear related apparatus which would benefit from an ear wax barrier.

The hearing aid includes a shell and a receiver within the shell. Both the shell and receiver include an acoustic output port. The barrier includes a housing with a plurality of projection and a variable acoustic attenuator. The housing interconnects the acoustic output ports of the receiver and shell. The housing defines an interior surface and a central axis of passage between said two ends of the housing.

The projections may be displaced from each other. Both extend inwardly from the interior surface of the housing. Each projection partially occludes a portion of the housing interior. Consequently, the projections provide a tortuous path for solid or semiliquid ear wax migrating axially along the inside of the housing. The variable acoustic attenuator and the projections provide a constricted passageway for damping of the acoustic response of the hearing aid.

Thus, an object of the present invention is an improved ear wax barrier for a hearing aid. Another object of the present invention is a barrier that more effectively resists wax clogging. Still another object is a barrier that more substantially blocks the migration of naturally occurring ear wax, thereby reducing the clogging of a hearing aid receiver. Still a further object is a wax barrier that presents less acoustic impedance to a receiver when placed between the receiver and the acoustic exit of the hearing aid.

Another object is a barrier that collects wax and need not be cleaned nor changed as frequently over the life of the hearing aid. Another object is a wax barrier that is inexpensive to make and maintain, thereby lowering the cost of hearing aids for consumers.

BRIEF DESCRIPTION OF THE DRAWING

A preferred embodiment of the present invention is described herein with reference to the drawing wherein.

DETAILED DESCRIPTION OF THE PREFERRED EMBODIMENTS

Referring to FIGS. 1–10, a preferred embodiment of the present invention is shown as an improved ear wax barrier, generally designated 20, for an "in the ear" or "canal" type hearing aid, illustratively designated 22.

So-called "custom" or generic hearing aids are designed to fit either in the bowl of the ear or, alternatively, in the ear canal itself. Prior to the development of such aids, however, hearing aids were designed to be worn behind the ear or elsewhere.

Figure 1:
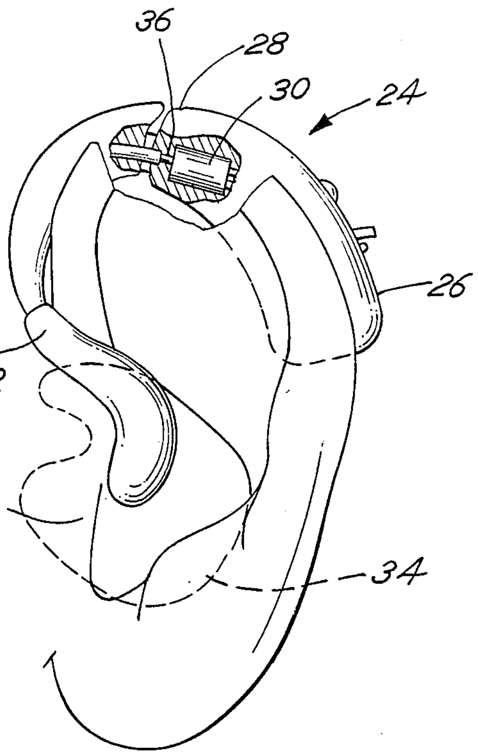
Fig. 1 (PRIOR ART)
FIG. 1 is a front, partially cut away view of a prior art behind-the-ear hearing aid, in use on a user's ear.

A prior art behind-the-ear hearing aid is shown in FIG. 1 and designated 24. The hearing aid, or "aid," 24 included a plastic case 26 to house the hearing aid components. Typical components included a microphone 28, amplifying circuitry (not shown), receiver 30, plastic tubing 32, and ear mold 34.

The microphone would receive a sound signal from outside the ear and convert it to an electrical signal. An electrical signal was then responsively transmitted to the receiver 30.

The receiver 30 included an acoustic output port 36 interconnected to the tubing 32. Upon receiving signals from the electrical components within the aid 24, the receiver 30 would transmit sound signals through its exit port 36. These sound signals were then conducted, via the tubing, to the ear mold 34 and the interior of the ear of the user.

In the prior art embodiment shown in FIG. 1, the acoustic exit port 36 of the receiver 30 was physically isolated from the ear environment by the tubing 32. As a result, the migration of the solid or semiliquid ear wax material into the receiver 30 was negligible due to the physical length of the tubing.

With the decreased size of electronic components in the 1970's and 1980's, however, more cosmetically attractive hearing aids could be constructed. Such aids fit in the ear or the ear canal of the user. See the aid 22, shown in FIG. 2.

Like the aid 24 shown in FIG. 1, the aid 22 also includes a shell 40 which may also include a microphone 42, amplification circuitry (not shown) and a receiver 44. The shell 40 and receiver 44 each include an acoustic output port, respectively designated 46, 48. The output ports 46, 48 of the shell 40 and receiver 44 are interconnected by a hearing aid sound channel 50. The barrier 20 is positioned in the channel 50 between the two acoustic output ports 46, 48.

Again, the microphone 42 receives sound signals and responsively transmits an electrical signal. An electrical signal, in turn, is sent to the receiver 44, which converts it to a sound signal. The sound signal is then transmitted, through the acoustic port 48 of the receiver 44, through the sound channel 50 of the aid 22, to the acoustic exit port 46 in the shell 40 of the hearing aid 22. After leaving the shell 40 of the aid 22, the sound may travel down the ear canal 52 of the user, to the ear drum.

Figure 2:
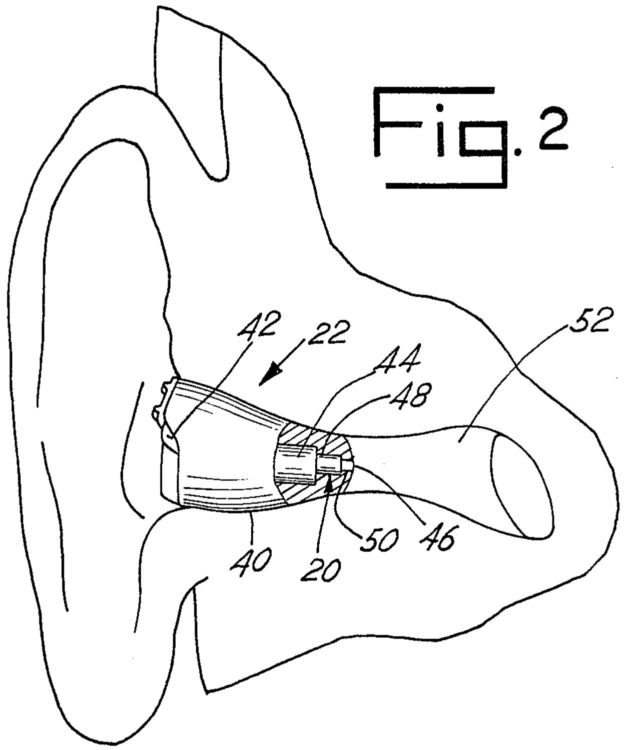
FIG. 2 is a right side, partially cut away view of a preferred embodiment of the present invention, showing an in-the-ear hearing aid with an ear wax barrier, in use within the user's ear.
Figure 3:
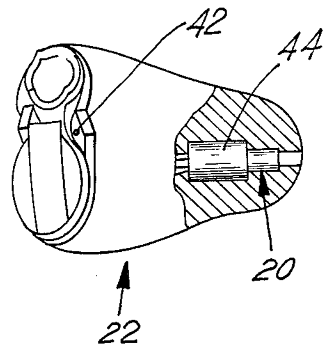
FIG. 3 is a perspective, partially cut away view of the preferred embodiment shown in FIG. 2.

As shown in FIG. 2, the receiver exit port 48 is in close proximity to the ear canal 52 containing wax generating tissue. As a result, wax frequently migrates through the exit port 46 in the shell 40, upward through the sound channel 50, and into the exit port 48 and the receiver 44 itself. This causes clogging of the receiver 44 or shell port 46, reducing its acoustic gain, power output, and occasionally the complete failure of the aid 22 to amplify or otherwise modify sound.

In a preferred embodiment of the present invention, the ear wax barrier 20 is interconnected between the receiver 44 and acoustic exit port 46 of the hearing aid shell 40, as shown in FIG. 2. For the preferred embodiment shown, the acoustic output port 48 of the receiver 44 is approximately cylindrical. Thus, the barrier 20 itself is substantially cylindrical, fitting snugly in the shell output port 46. See FIG. 3. In other embodiments, of course, that barrier 20 may have most any cross sectional configuration. Thus, for example, the barrier 20 could be made a part of the hearing aid 24. That is, the barrier 20 may be assembled as a part of the shell 40 or as a part of the receiver 44.

Figure 4:
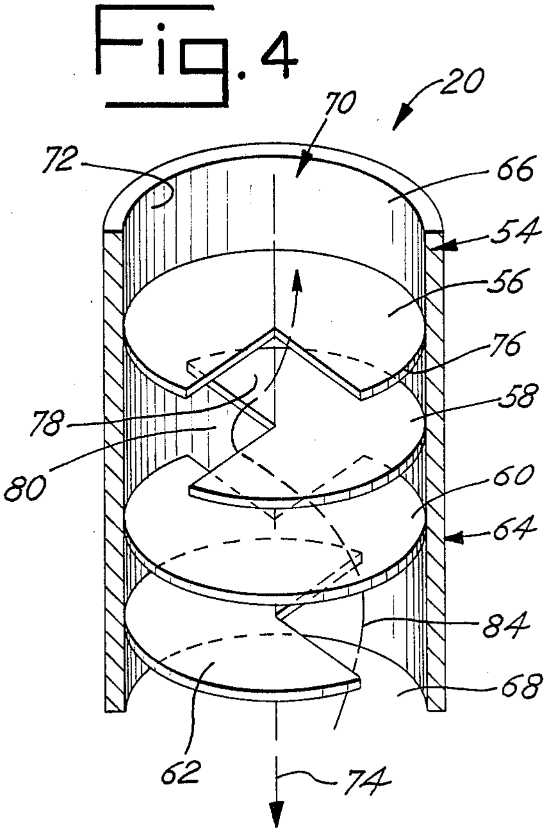
FIG. 4 is a perspective, partial cross-sectional view of the ear wax barrier shown in FIG. 3.

As shown in FIG. 4, one embodiment of the ear wax barrier 20 includes a housing 54 and first, second, third and fourth projections, respectively designated 56, 58, 60, 62. Of course, a lesser or greater number of projections may be used.

The housing 54 in this embodiment is substantially cylindrical, defining a wall 64 with first and second ends 66, 68 and comprised of any variety of materials. In the preferred embodiment, injection molded thermoplastic is used. Examples of materials that might be used to make the housing include "Cycolac," and ABS (Acrylonitrile-Butadiene-Styrene) resin.

The dimensions of the one particular embodiment of the invention herein described follow. Of course, alternative embodiments are possible, and the dimensions should not be read to limit the scope of the present invention.

The housing 54 defines a length, between the first and second ends 66, 68, of approximately 0.35 inch, and the inside diameter of the housing 54 is approximately 0.11 inch. The thickness of the housing wall is approximately 0.01 inch, and the housing 54 further defines an interior chamber 70 and an interior surface 72. In addition, the housing 54 defines a central axis of passage 74 between the first and second ends.

In the one preferred embodiment herein described, the central axis 74 passes through the center of a roughly cylindrical housing 54, substantially equidistant at all points from the interior surface 72 of the housing 54. The first end 66 fits snugly into the receiver exit port 48. The second end 68, distal from the receiver 44 when in use in a hearing aid 22, faces the acoustic exit port 46 of the hearing aid shell 40 and the interior of the user's ear.

As shown, each of the four projections 56–62 is substantially similar to the others. (Of course, a single barrier could also use a variety of differently shaped projections.) Only the first projection 56 is discussed in detail below for illustrative purposes.

The projection 56 is attached to the interior surface 72 of the housing 54 and extends inwardly toward the central axis 74 of the housing 54. The projection 56 partially occludes the central acoustical passageway or interior housing chamber 70.

In the preferred embodiment, the projection 56 is comprised of a thermoplastic that can be injection molded, just as the housing 54 is. In an alternative embodiment, of course, the projection 56 could also be covered with a coating that exhibits a low cohesion to cerumen. Such coatings include, for example, "Teflon" and "Tefzel." Such a coating could make any projection or housing easier to clean after wax has built up upon it.

If the housing 54 is cylindrical, the projection 56 defines an outside perimeter 76, a portion of which resembles a circle. Alternatively, the projection 56 may be described as a disk. While the invention encompasses a variety of projection shapes, the preferred embodiment of FIG. 4 includes a disk having a wedge-shaped gap 78. In this one preferred embodiment, the projection 56 defines a maximum outside diameter of approximately 0.11 inch, so that it fits tightly against the interior surface 72 of the housing 54.

In the preferred embodiment, the projection 56 is attached to the interior surface 72 of the housing 54. In the preferred embodiment, the attachment is accomplished with strong glue such as a cyanoacrylate ester. In alternative embodiments, however, the projection 56 could be molded as part of the housing 54, or alternatively, simply press fit into the interior chamber 70 of the housing 54, or otherwise attached to the housing 54.

The housing 54 in the preferred embodiment defines an interior cross-sectional area of a circle and circle interior. Again, a portion of the circle interior is occluded by the projection 56. In the preferred embodiment shown in FIG. 4, the projection 56 is in the shape of a disk with a wedge 78 removed. The "removed" portion is described as a "wedge" 78 for purposes of illustration. It is to be understood, of course, that while a wedge typically has only straight sides, the wedge 78 defining an open area in the present context may also include one rounded side missing from the rounded projection 56, shown in FIG. 4.

Using alternative terminology, the projection 56 may be described as a "270° circle portion." The central axis 74 of the housing 54 defines the center point of the circle. Also, the "gap" from the projection 56, may be described as a 90° circle portion.

The open wedge 78 of the projection 56 defines an open area in the cross-sectional area of the housing 54. Thus, if one were looking through the housing from the first end 66 toward the second end 68, parallel to the axis 74, the interior of the housing 54 would define a circle interior. The projection 56 would block the interior 76 of the housing 54 except for the wedge 78. The first projection 56 itself defines a first occluded area and the wedge 78 defines a first open area in the cross-sectional area of the housing 54, normal to the axis 74.

It is through this open area, or wedge 78, in the housing 54 that sound may travel from the receiver 44 to the exterior of the aid 22. If this projection 56 were the only barrier, however, wax, under some circumstances, might flow through the open area. Thus, at least the one additional, second projection 58 is usually provided to prevent further passage of ear wax.

In the preferred embodiment, the second projection 58 is placed approximately 0.02 inch away from the first projection 56. Applicant has found that, in the most preferred embodiments, the projections should be placed apart enough so that the projections will not substantially effect the overall acoustic response and the amount of expected wax buildup will be less than the distance between the projections. Thus, spacing between the projections of 0.005 inch to 0.04 inch may be used for the most preferred performance of the wax barrier 20.

In the preferred embodiment shown, the projections 56-62 are interdigitated within the housing 54, i.e., the projections are spacially and angularly displaced with respect to the central axis 74. The projections could be made of a variety of substances, such as, for example, the thermoplastic or semipermeable material. Of course, the projections may be radially or axially displaced from each other.

The second projection 58 is like the first projection 56 in that it defines a second wedge 80. While the second wedge of the preferred embodiment has the same shape as the first wedge 78, the second wedge 80 may, of course differ in size and shape of any other wedge. The second projection 58 and the second wedge 80 also define an occluded area and an open area in the housing, normal to the axis 74. The open area of the second projection 58 is positioned over the first occluded area. Thus, a tortuous path is provided for wax which would otherwise migrate from the first end 66 to the second end 68.

For the preferred embodiment shown in FIG. 4, the wedges 78, 80 measure approximately 90°. The second projection 58 is similar to the first projection 56 in design, but has been rotated clockwise 90° from the position of the first projection 56. FInally, the fourth projection 62 has been rotated 90° in a clockwise direction from the position of the third projection 60.

In the preferred embodiment shown in FIG. 4, the open area of each projection is further blocked, or occluded, by occluding portions of three other projections. The interdigitated projections thus cooperate to completely occlude the acoustical passageway 70 against wax migration. That is, every line of migration through the housing 54 along the interior surface 72 is interrupted by a projection. Applicants have found that such a construction provides a tortuous path for ear wax, substantially reducing the amount of ear wax that may migrate from the sound channel 50 to the receiver 44 while, at the same time, providing substantially little acoustic impedance to the receiver 44.

Figure 5:
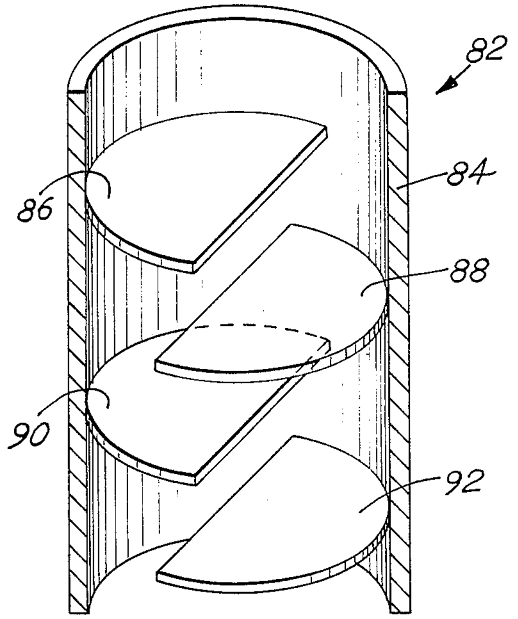
FIG. 5 is a perspective, partial cross-sectional view of a first alternative embodiment of the ear wax barrier shown in FIG. 4.

A second embodiment of the preferred invention is disclosed in FIG. 5. The barrier 82 includes a housing 84 and a multiplicity of projections. The barrier 82 includes first, second, third, and fourth projection 86, 88, 90, 92. Construction of the housing 84 is similar to that shown in FIG. 4. Also, the projections 86-92 are of substantially the same thickness and positioned substantially the same distance apart as the embodiment shown in FIG. 4. However, rather than being 270° circle portions, each projection is substantially a 180° circle portion (or semicircle).

The first projection 86 again defines a first occluded area and a first open area. The second projection 88 has been effectively rotated such that the occluded area of the second projection blocks the open area of the first projection 86. The third projection 90 blocks the open area of the second projection 88. Similarly, the fourth projection 92 blocks the open area of the third projection 90.

Figure 6:
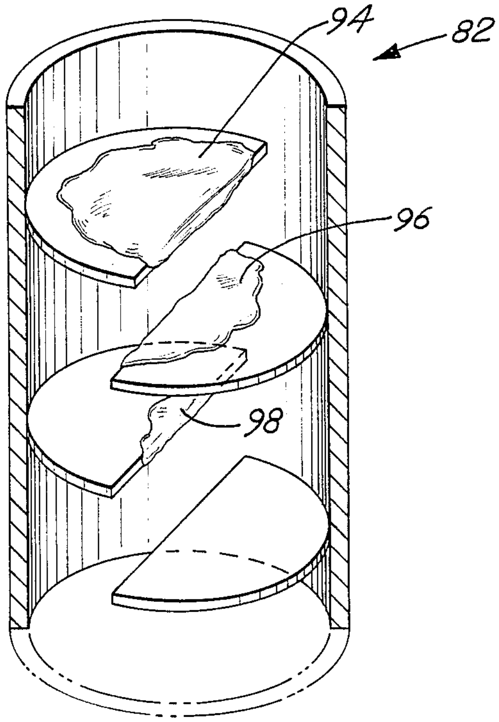
FIG. 6 is a perspective, partial cross-sectional view of the preferred embodiment shown in FIG. 5, showing a buildup of ear wax after the barrier has been in use within a hearing aid.

As shown in FIG. 6, such an arrangement of 180° circle portion projections 86-92 prevents wax from flowing directly through the housing 84. A substantial buildup of wax 94 may be anticipated on the first projection over the life of the hearing aid 22. The second projection 88 may be expected to receive a lesser amount of wax buildup 96, since it is positioned slightly deeper into the housing 84. The third projection 90, however, experiences substantially smaller amounts of wax buildup 98, since the path for wax migration has been blocked by the first and second projections 86, 88. The fourth projection 92 receives even less wax buildup, because of the wax already blocked by the first three projections 86-90.

Figure 7:
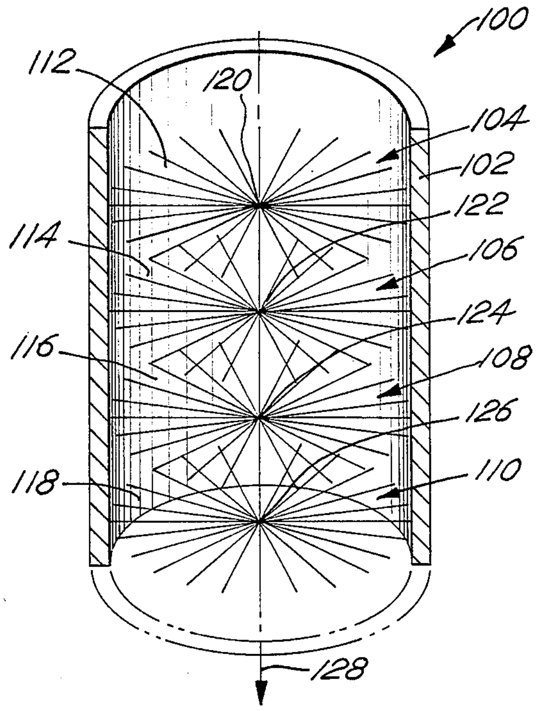
FIG. 7 is a perspective, partial cross-sectional view of a second, alternative embodiment of the ear wax barrier shown in FIG. 4.

Yet another embodiment of the present invention shown in FIG. 7. The barrier 100 again includes a housing 102 and a multiplicity of projections 104, 106, 108, 110. The housing is substantially similar to that shown in FIGS. 4-6.

Each of the four projections 104-110 is comprised of a series of 24 spokes 112, 114, 116, 118, radiating from central points 120, 122, 124, 126 defined by the central axis 128. Each spoke is approximately 0.01 in diameter. In the preferred embodiment, of course, the projections 104-110 are again made of plastic, and the second projection 106 is effectively rotated a few degrees from the position of the first projection 104. In turn, the third projection 108 has been rotated slightly from the position of the second projection 106, and the fourth projection 110 has a position rotated slightly from the position of the third projection 108.

Figure 8:
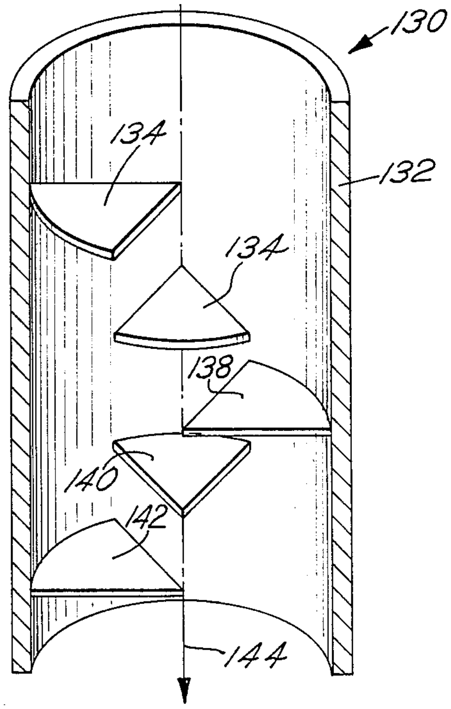
FIG. 8 is a perspective, partial cross-sectional view of a third, alternative embodiment of the ear wax barrier shown in FIG. 4.

Yet another alternative embodiment is shown in FIG. 8. In this embodiment, the barrier 130 includes a housing 132 and first, second, third, fourth, and fifth projections, 134, 136, 138, 140, 142. Each of the projections 134-142 comprises approximately a portion of a circle portion. The second projection 136 has been rotated from that of the first projection 134. The third, fourth and fifth projections 138-142 are similarly rotated from the position of each other previous projections. When the housing is viewed from the direction of the arrow of the axis 144 shown in FIG. 9, the entire internal cross-sectional area of the housing is again blocked by the projections 134-142.

The plurality of projections 134-142 have approximately the same thickness and displacement along the axis 144 as the projections previously described for the embodiment shown in FIGS. 4-7. There are five, rather than four, projections however. Thus, the housing 132 is approximately 0.02 inch longer than the housing 54 shown in FIG. 4.

Figure 9:
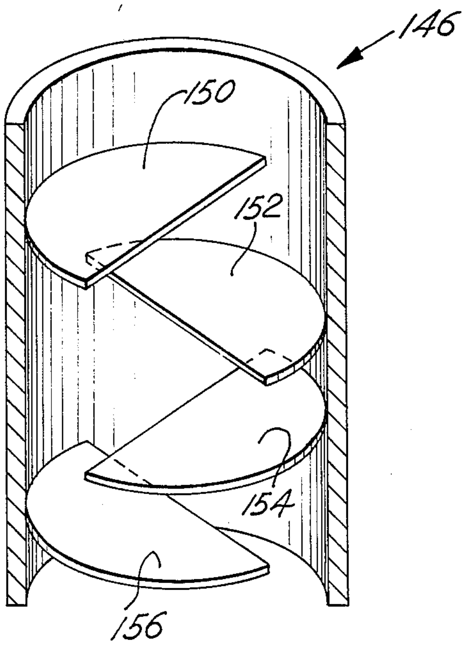
FIG. 9 is a perspective, partial cross-sectional view of a fourth, alternative embodiment of the ear wax barrier shown in FIG. 4.

Yet another alternative embodiment is shown in FIG. 9. Like the embodiment shown in FIG. 5, the barrier 146 includes a housing 148 and a plurality of projections 150, 152, 154, 156, and each of the projections 150-156 are approximately 180° circle portions. However, each projection is rotated approximately 90° (rather than 180°) from the preceding projection. Thus, the second projection 152 has been rotated approximately 90° from the position of the first projection 150. The third and fourth projections 154, 156 are also rotated approximately 90°.

Figure 10:
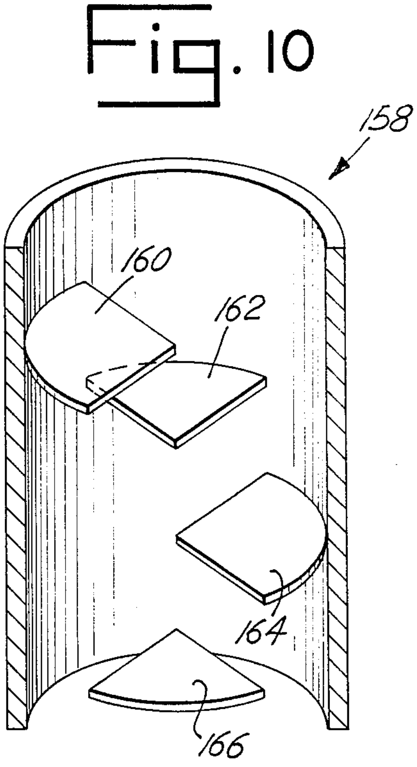
FIG. 10 is a perspective, partial cross-sectional view of a fifth, alternative embodiment of the ear wax barrier shown in FIG. 4.

A further preferred embodiment shown in FIG. 10. Each of the projections 160-166 comprises approximately a 90° circle portion. The second projection 162 has been rotated approximately 90° from the position of the first projection 160. Similarly, the third projection 164 is rotated approximately 90° from the position of the second projection 162. The fourth projection 166 has a position which is rotated approximately 90° from the position of the third projection 164.

Figure 13:
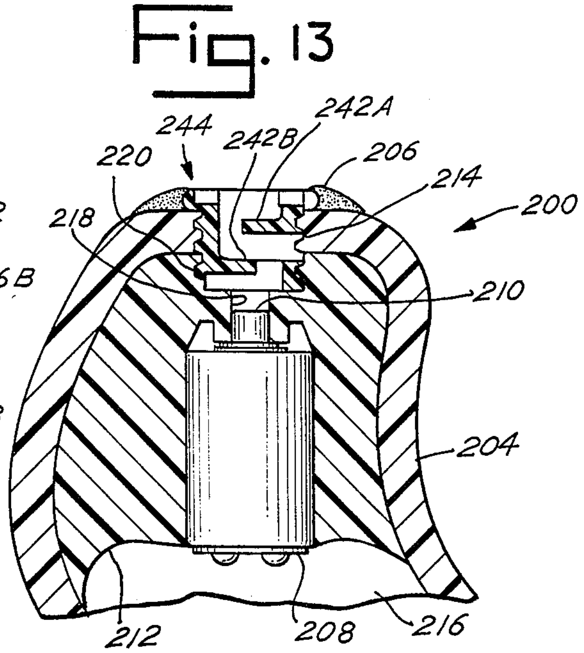
FIG. 13 is a partial cross-sectional, partial side view of a hearing aid illustrating the ear wax barrier of FIG. 11 incorporated therein.

A sixth preferred embodiment of the present invention is shown in FIGS. 11-15 as an ear wax barrier 200 for a hearing aid 202. As best shown in FIG. 13, the hearing aid 202 includes a shell 204 adapted to be inserted in an ear channel (not shown) and defining an acoustical outlet port 206. The hearing aid 202 further includes a receiver 208 having a receiver outlet port 210.

In this preferred embodiment, the receiver 208 is secured within the shell 204 by an elastomeric filling 212. That is, the receiver 208 is positionally set with respect to the shell 204 and then embedded in the filling 212. Once to filling 212 cures, the receiver 208 is secured as well as protected by the pliable, shock-absorbing filler 212.

The shell 204 includes an internally threaded opening 214 which interconnects the acoustical outlet port 206 with the interior chamber 216 of the shell 204. This opening 214 is adapted to receive the ear wax barrier 200. As best shown in FIG. 13, the shell 204 is filled in such a manner that the elastomeric filler 212 defines a substantially cylindrical channel 218 immediately adjacent the receiver outlet port 210 and an internally-threaded cavity 220 immediately adjacent and extending the opening 214 into the interior chamber 216.

In this preferred embodiment, the ear wax barrier 200 is an integral piece of molded thermoplastic material, such as ABS. The barrier 200 includes a substantially cylindrical housing 222 defining a central acoustical passageway 224 between a barrier inlet port 226 and a barrier outlet port 228. The housing 222 has an externally-threaded portion 230 and a collar portion 232, which defines the outlet port 228. As shown, the outer diameter of the collar portion 232 is slightly greater than the outer diameter of the externally-threaded portion 230.

The housing 222 is adapted to be received by the internally-threaded opening 214 of the shell 204, as extended by the filler 212. Secured therein, the central axis 234 of the housing 222, or more particularly the central acoustical passageway 224, substantially aligns with the receiver outlet port 210. The barrier inlet port 226 aligns with and slightly overlays the channel 218, such that audio signals produced by the receiver 208 are received by the barrier 200 and pass through the acoustical passageway 224. This is, the passageway acoustically links to receiver 208 to the outlet 206 of the hearing aid 202.

In this preferred embodiment, the collar portion 232 of the housing 222 includes diametrically opposed slots 236A, 236B, extending from the substantially cylindrical barrier outlet port 228. These slots 236A, 236B cooperate to define key means, generally designated 238, for rotating the ear wax barrier 200 with an instrument having a screwdriver-like configuration (not shown). Utilizing the key means 238, the ear wax barrier 200 can be readily removed from the shell 204 for cleaning or replacement.

Figure 11:
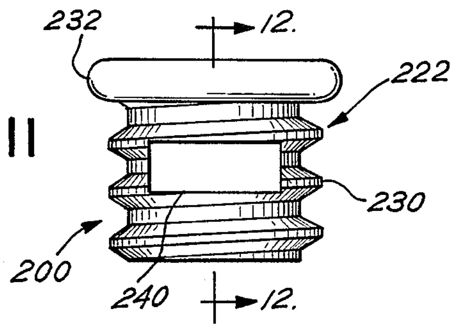
FIG. 11 is a side view of a sixth, alternative embodiment of the present invention.
Figure 12:
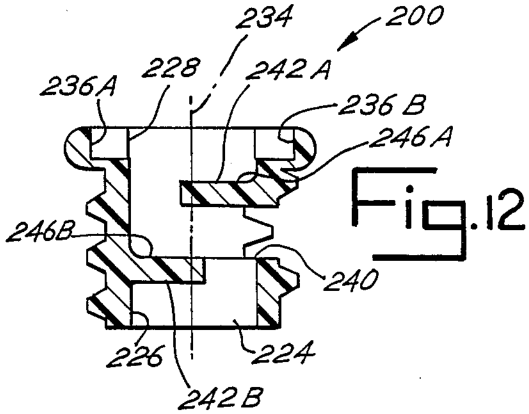
FIG. 12 is a cross-sectional view of the ear wax barrier shown in FIG. 11 taken along line 12—12.

The ear wax barrier 200 or more particularly the externally-threaded portion 230 of the housing 222 includes an access opening 240. As best shown in FIGS. 11 and 12, the access opening 240 is substantially rectangular and substantially centrally located in the externally-threaded portion 230. The access opening 240 provides direct access to the passageway 224 for inspection and cleaning.

Figure 14:
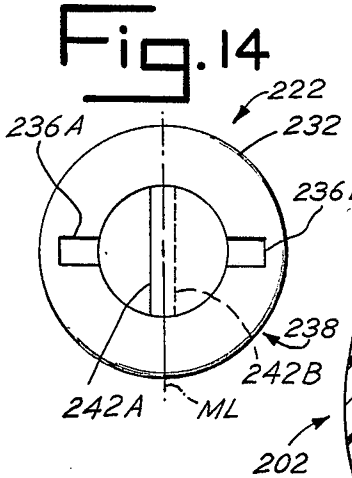
FIG. 14 is a top view of the ear wax barrier of FIG.. 11.

Referring now to FIGS. 12 and 14, the ear wax barrier 200 also includes at least two substantially semi-circular projections 242A, 242B, which extend into the passageway 224. The projections 242A, 242B are equally spaced from each other and from the barrier inlet port 226 and outlet port 228 and are substantially perpendicular to the central axis 234 and the interior wall surface of the housing 222. In this preferred embodiment, the projections 242A, 242B extend slightly beyond the midline "ML" of the collar portion 232 (as shown best in FIG. 14), such that the projections 242A, 242B slightly overlap.

The projections 242A, 242B (here and in the other preferred embodiments) interrupt the central acoustical passageway 224 such that the migration of ear wax is retarded. The projections 242A, 242B cooperate to define trap means, generally designated 244, for accumulating ear wax in predetermined accumulation sites 246A, 246B, thereby retarding flow through the central acoustical passage 224 without substantial interference with the performance characteristics of the hearing aid 202. As best shown in FIG. 14, the accumulation sites 246A, 246B, in cooperation, extend completely about the interior wall surface of the housing 222.

Figure 15:
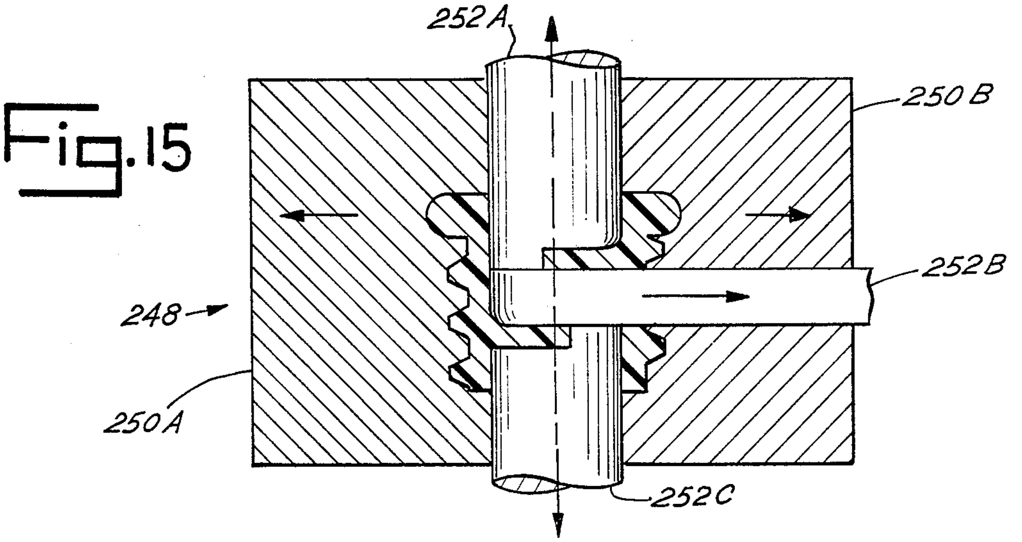
FIG. 15 is a partial cross-sectional, partial side view of a mold to produce the ear wax barrier of FIG. 11.

The ear wax barrier 200 is molded in a five-part mold 248 shown in FIG. 15. The mold 248 includes mold halves 250A, 250B adapted to receive first, second and third inserts 252A, 252B, 252C. As shown, the three inserts 252A, 252B, 252C cooperate to define the central acoustical passageway 224 and access opening 240.

Figure 16:
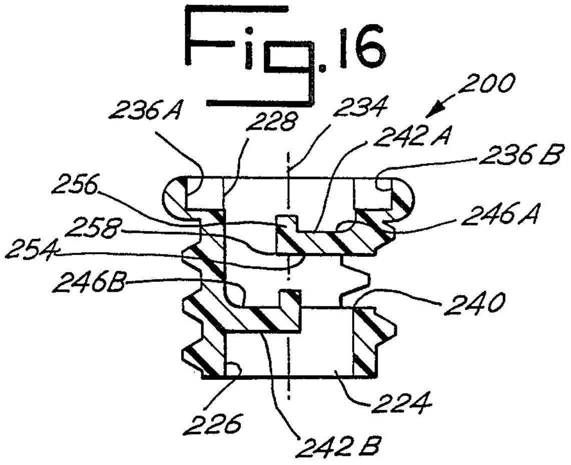
FIG. 16 is the cross-sectional view of FIG. 11 illustrating a modified projection for the ear wax barrier.
Figure 17:
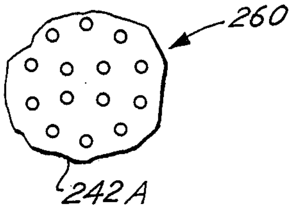
FIG. 17 is a partial top view of the modified projection shown in FIG. 16.

Referring now to FIGS. 16 and 17, a modified configuration for the projections 242A, 242B is shown. (Only one projection 242A is discussed herein for simplicity.) The projection 242A includes a disk portion 254 and a flange portion 256. The disk portion 254 is identical to the projection 242A described above and shown in FIGS. 12-15. The disk portion 254 defines a terminus edge 258.

The flange portion 256 extends from the terminus edge 258, substantially perpendicular to the disk portion 254. The flange portion 256 extends away from the receiver 208 and towards the acoustical outlet port 206 of the shell 204. The flange portion 256 creates further impedance to the migration of wax through the barrier 200 and cooperates with the disk portion 254 to define the trap means 244.

The disk portion 254 includes a series of depressions of "dimples", generally designated 260, which further retard wax migration by providing additional accumulation sites. In essence, migration is retarded since the depressions 260 must be at least partially filled before further advancement occurs.

The projection 242A shown in FIG. 16 offers an additional advantage. The configuration of the disk portion 254 and flange portion 256 provides an adjustable acoustic damping means and may, with proper dimensioning, provide substantially optimum damping of the overall frequency response, in combination with the wax barrier 200. In one embodiment, the flange portion 256 is connected to the disk portion 254 by a "living hinge". The orientation of the flange portion 256 is adjusted to provide a variably constricted acoustic pathway, thus providing the desired acoustic damping in combination with the wax barrier 200. Once properly positioned, the flange portion 256 is secured to the interior wall surface of the housing 222 by gluing or other means.

Figure 18:
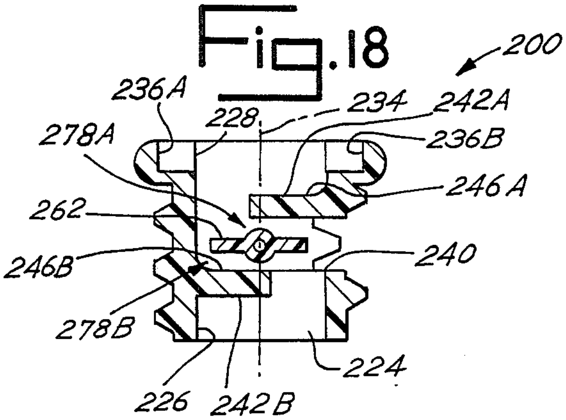
FIG. 18 is the cross-sectional view of FIG. 11 illustrating incorporation of an acoustical baffle.
Figure 19:
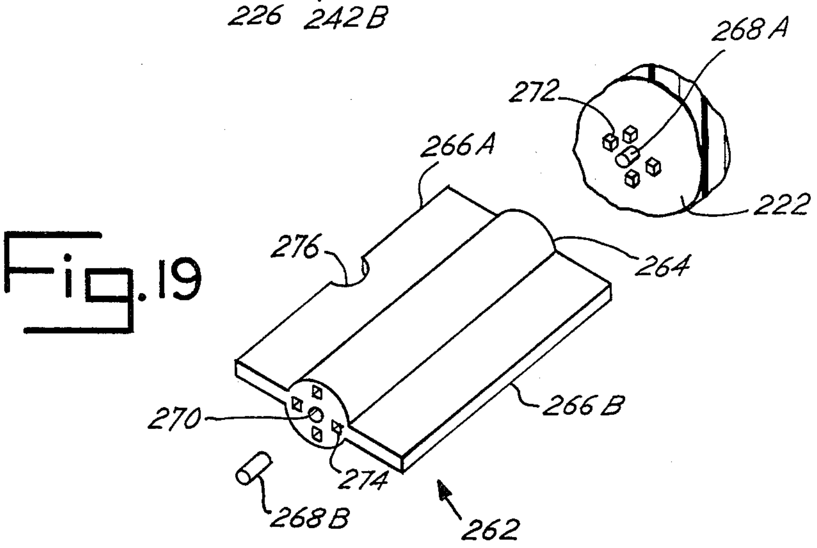
FIG. 19 is an enlarged, partial and exploded perspective view of the housing and acoustical baffle shown in FIG. 18.

As shown in FIGS. 18 and 19, the ear wax barrier 200 may also include an adjustable acoustical baffle 262. The adjustable baffle 262, or "variable acoustic attenuator", includes a central, substantially cylindrical section 264 and a pair of wing sections 266A, 266B, which extend in opposed relationship from the central section 264. Each of the wing sections 266A, 266B is substantially rectangular and thin. The adjustable baffle 262 is mounted on opposed pins 268A, 268B which extend from the interior wall surface of the housing 222 and engage the channel 270 defined by the central section 264. The orientation of the adjustable baffle 262 may be set by gluing or by mated, interlocking tabs 272 on the interior wall surface of the housing 222, equally spaced about the pins 268A, 268B, and slots 274 equally spaced about the ends of the central section 264 of the adjustable baffle 262. The adjustable baffle 262 includes an adjustment aperture 276, baffle 262. The adjustable baffle 262 includes an adjustment aperture 276, centrally located along one side of one of the wing sections 266A, 266B. The open areas 278A, 278B between the adjustable baffle 262 and the projections 242A, 242B provide a constricted passageway for damping of the overall acoustic response.

In each of the embodiments described, a tortuous path is provided to effectively reduce wax migration. Moreover, in some instances, the embodiment also includes a means for adjusting the overall acoustic damping in combination with the wax barrier 200. Nonetheless, substantial open areas are provided to reduce acoustic impedance by the wax barrier. In each of the preferred embodiments, the cross-sectional area of the housing is substantially blocked off by one or more projections.

In the preferred embodiments previously described, the wax barrier 20 is placed in the sound channel 50 or otherwise positioned between the output port 46 of the hearing aid shell 30 and the output port 48 of the receiver 44. Such positioning allows the barrier 20 to block wax from entering the receiver 44 from the outside of the hearing aid 22. Of course, it is understood that, as an alternative embodiment the wax barrier 20 may be interconnected directly to or into the output port 48 of the receiver 48.

Various preferred embodiments of the present invention have been described herein. It is to be understood, of course, that changes and modifications may be made in the embodiments without departing from the true scope and spirit of the present invention as defined by the appended claims.

I claim:

1. An ear wax barrier for a hearing aid, said hearing aid including a shell having an acoustical outlet and a receiver positioned within said shell, said receiver having a receiver outlet port, comprising, in combination:

a housing adapted to be received by said shell, said housing including a substantially cylindrical, central acoustical passageway linking said acoustical outlet and said receiver outlet port, said substantially cylindrical, central acoustical passageway defining a central axis and being defined by an interior wall surface of said housing;

a plurality of projections within said substantially cylindrical, central acoustical passageway, said projections being spatially and angularly displaced with respect to said central axis and cooperating to occlude said substantially cylindrical, central acoustical passageway, said projections being substantially perpendicular to said central axis and said interior wall surface;

said projections cooperatively defining trap means for providing wax accumulation sites within said housing, whereby migration of ear wax into said hearing aid is substantially retarded; and a variable acoustic attenuataor, said variable acoustic attenuator and said projections cooperatively defining means for damping the acoustic response of said hearing aid wherein said acoustic response of said hearing aid may be adjusted by said variable acoustic attenuator.

2. An ear wax barrier as claimed in claim 1 wherein said variable acoustic attenuator includes an adjustable baffle having a pair of wing sections to adjustably constrict said central acoustical passageway.

3. An ear wax barrier as claimed in claim 1 wherein said housing includes an access opening between said projections, said access opening providing access to said substantially cylindrical, central acoustical passageway.

4. An ear wax barrier as claimed in claim 1 wherein said housing includes a collar portion and an externally threaded portion, said externally threaded portion to be received by a threaded portion of said shell.

5. An ear wax barrier as claimed in claim 1 wherein said collar portion includes key means for rotating said housing, whereby said housing may screwed into and out of said shell.

6. An ear wax barrier as claimed in claim 1 wherein said key means includes two opposed slots.

* * * * *